(12) United States Patent
Tiemann

(10) Patent No.: US 6,286,622 B1
(45) Date of Patent: Sep. 11, 2001

(54) HEARING PROTECTOR

(75) Inventor: Rudi Peter Tiemann, Hellevoetsluis (NL)

(73) Assignee: Simply Silence Simsin B.V., Sh Oud Gastel (NL)

( * ) Notice: Subject to any disclaimer, the term of this patent is extended or adjusted under 35 U.S.C. 154(b) by 0 days.

(21) Appl. No.: 09/613,772

(22) Filed: Jul. 11, 2000

Related U.S. Application Data

(63) Continuation of application No. PCT/NL99/00031, filed on Jan. 18, 1999.

(30) Foreign Application Priority Data

Jan. 19, 1998 (NL) .................................... 1008065
Jan. 19, 1998 (NL) .................................... 1008066

(51) Int. Cl.$^7$ .................................................. A61B 7/02
(52) U.S. Cl. .......................................... 181/135; 128/864
(58) Field of Search ................................ 181/135, 129, 181/130, 131, 132, 134, 137; 128/864, 868

(56) References Cited

U.S. PATENT DOCUMENTS

| | | | | |
|---|---|---|---|---|
| 3,934,100 | * | 1/1976 | Harada | 181/135 |
| 4,540,063 | | 9/1985 | Ochi et al. . | |
| 5,113,967 | * | 5/1992 | Killion et al. | 181/135 |
| 5,332,871 | * | 7/1994 | Carrigan | 181/135 |
| 5,887,070 | * | 3/1999 | Iceberg et al. | 181/130 |
| 6,082,485 | * | 7/2000 | Smith | 181/135 |

FOREIGN PATENT DOCUMENTS

| | | |
|---|---|---|
| 22 36 112 A | 1/1974 | (DE) . |
| 40 08 982 A | 11/1993 | (DE) . |
| G 93 13 061.9 | 11/1993 | (DE) . |
| 0 244 979 A | 11/1987 | (EP) . |
| 0 336 487 A | 10/1989 | (EP) . |
| 2 173 110 A | 10/1986 | (GB) . |
| 9 401 212 A | 3/1996 | (NL) . |

* cited by examiner

*Primary Examiner*—Khanh Dang
(74) *Attorney, Agent, or Firm*—Hoffmann & Baron, LLP

(57) ABSTRACT

A hearing protector, including a sealing body with a channel, and a muffling device which is connected to the sealing body and connects to the channel. When the sealing body is placed in an auditory canal, the channel extends between the auditory canal and the atmosphere. The channel has a distal end part at the side of the auditory canal and a proximal end part at the side of the atmosphere. The muffling device connects to the proximal end part of the channel and includes a rotatable control element, provided with at least one through aperture. The muffling device also includes a housing element provided with at least one through aperture. The control element and the housing element are rotatable relative to each other between two or more discrete rotation positions with corresponding muffling value. The apertures in the control element and the housing element overlap each other to a greater or lesser extent depending on a mutual angle of rotation.

12 Claims, 5 Drawing Sheets

HEARING PROTECTOR

CROSS-REFERENCE TO RELATED APPLICATIONS

This application is a continuation of copending application International Application No. PCT/NL99/00031, filed on Jan. 18, 1999, and which designated the U.S.

FIELD OF THE INVENTION

The invention relates to a hearing protector intended for placing in an auditory canal of a user. The hearing protector includes a sealing body with a channel extending through it and a muffling device which is connected to the sealing body and connects to the channel. The sealing body is adapted to be placed in an auditory canal, so that the channel extends between the auditory canal and the atmosphere, in which the channel has a distal end part at the side of the auditory canal and a proximal end part at the side of the atmosphere. The muffling device connects to the proximal end part of the channel and comprises a rotatable control element, which control element is provided with at least one through aperture. The muffling device further comprising a housing element, which housing element is provided with at least one through aperture, the control element and the housing element being rotatable relative to each other between rotational positions with a corresponding muffling value, with the result that the apertures in the control element and the housing element overlap each other to a greater or lesser extent depending on a mutual angle of rotation.

BACKGROUND OF THE INVENTION

Such a hearing protector is known from DE-A-40 08 982, which discloses a substantially solid sealing body which is made to measure for a particular user (otoplastic). The sealing body contains an aeration channel which is widened at the proximal end part. A muffling device is fitted in the widened end part. The muffling device consists of a cylindrical element which is provided with a through aperture. The through aperture is made eccentrically in the element, the diameter of the aperture corresponding approximately to the diameter of the aeration channel. On the front side, the element is provided with a slot in which a screwdriver can engage. In this way, the element can be rotated relative to the sealing device, with the result that the aeration channel is cleared to a greater or lesser extent by the through aperture.

A disadvantage with this known hearing protector is that the muffling device is difficult to control. If a specific muffling value is desired, said value is difficult or impossible to set or distinguish. The design of the muffling element is intended in particular for otoplastics, and it is ill suited for use on a hearing protector with a sealing body of a more open design intended for universal use. In the open position of the muffling device, inadequate sound muffling can be achieved as a result of the relatively large diameter of the through aperture in the cylindrical element. In the fully closed position of the muffling device, undesired acoustic leakage still occurs. Moreover, the muffling device cannot be controlled without an aid.

EP-A-0 333 298 and DE-U-93 13 061 disclose hearing protectors with muffling devices, in which the muffling device comprises a housing which is fixed in the channel of the sealing body and comprises a central bore, consisting of a cylindrical threaded part and a part which tapers in the distal direction. A correspondingly threaded adjusting pin, which is formed such that it is complementary to the tapering part of the bore, fits into the bore, which pin can be moved in the axial direction by rotation in the bore, with the result that the passage to the open environment can be adjusted. This permits a stepless adjustment of the passage, and thus of the muffling action of the muffling device. Said stepless adjustment of the muffling action is used for having the muffling action set once by a manufacturer, by way of measurement, at a value specified by a user.

As in the case of DE-A-40 08 982, it is also a disadvantage in this type of hearing protector that the muffling device is difficult to control. Any change in the muffling value to a different muffling value will usually have to be carried out again by the manufacturer by means of rotating the adjusting pin and at the same time measuring the muffling value. The setting of the muffling value will generally not be changed by the user. However, if the user still changes the setting of the muffling device himself, it will have to be carried out by feel, and there is a risk here that a muffling effect which is correct by feel will turn out to be too low a muffling value in certain circumstances, so that the user, without noticing it, runs the risk of hearing loss in the long run.

SUMMARY OF THE INVENTION

The object of the present invention is to overcome the abovementioned disadvantages, and in particular to provide a hearing protector in which several desired muffling values of a muffling device can be adjusted quickly, reliably and in a reproducible manner by a user himself. Another object of the invention is to provide a muffling device which is suitable for combining with a sealing body designed for universal use.

These objects are achieved according to the invention including a hearing protector. The muffling device comprises a housing element which has at least one through aperture. The elements are rotatable relative to each other between two or more discrete rotation positions with corresponding muffling values. In the discrete rotation positions the apertures in the elements overlap to a greater or lesser extent, depending on the mutual angle of rotation. Various specific muffling values, determined in advance by a manufacturer, can advantageously be set by the user himself in a simple and reproducible manner. The dimensions of the muffling device do not change when the muffling device is adjusted to another muffling value set during use. This provides a very compact hearing protector with adjustable muffling value. The control element and the housing element are provided with complementary position-indicating means, for indicating the two or more discrete rotation positions. Herewith the complementary position-indicating means comprise parts which, through a rotation of the elements relative to each other, snap or click into each other. The muffling device in each case can be rotated until a click is heard and/or felt by the user, which indicates that the muffling device is situationed in a discrete rotational position. If desired, the rotation of the muffling device may also be carried out when the hearing protector is in the user's ear.

The hearing protector with the muffling device according to the invention is suitable in particular for use with a sealing body suitable for universal use. Such sealing bodies are known in many forms; see, for example, NL-A-94 01 212 and U.S. Pat. No. 4, 540 063. However, there is still room for improvement in the wearing comfort and the muffling characteristics of these known sealing bodies. The present invention now provides a hearing protector with a muffling device in which a sealing body is provided which, on the one hand, gives optimum wearing comfort and, on the other hand, in the specific combination with the muffling device according to the invention results in desired muffling characteristics. To this end, the sealing body comprises a central tube having a channel therein, at least one shell provided on the tube and designed to rest in a sealing manner against an auditory canal, and an end wall bounding the distal end part of the channel and having an end edge part of elastically deformable material which is bent inwards in the radial direction. In this case the end edge part is dimensioned in such a way that it deforms elastically in the axial direction under an axial pressure load, for example as a result of fitting the sealing body in an auditory canal. Thus a hearing protector is provided having a universal sealing body made of a flexible plastic which can shut off the auditory canal of different persons without in the process exerting unpleasant or painful pressure on the walls of the auditory canal. With the hearing protector designed in this way, the readily deformable front wall part of the sealing body will yield in the optimum manner, while effective insertion of the earplug body in the auditory canal is still ensured.

BRIEF DESCRIPTION OF THE DRAWINGS

The invention will be explained in greater detail below with reference to an exemplary embodiment shown in the drawing, in which.

DESCRIPTION OF THE PREFERRED EMBODIMENTS

Figure 1:
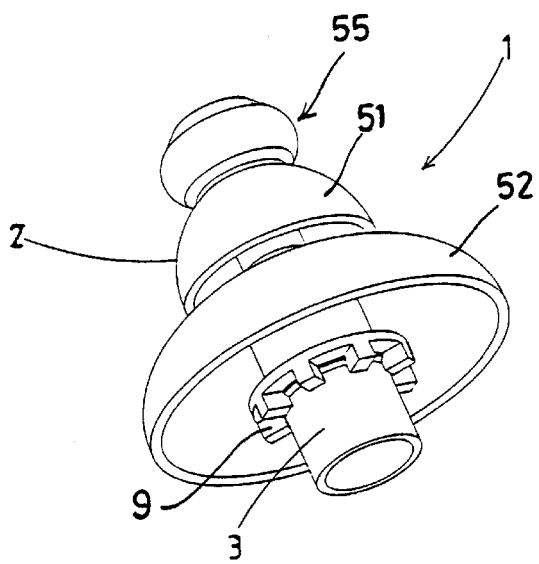
FIG. 1 is a view in perspective of a hearing protector according to the invention.

The hearing protector is indicated in its entirety by the reference numeral 1 in FIG. 1, and comprises a sealing body 2 and a muffling device 3. The sealing body will be explained in further detail below. The sealing body 2, which is made from a flexible material, for example a thermoplastic elastomer, is intended for placing in an auditory canal of a user. The sealing body 2 is designed in such a way that when placed in the auditory canal of the user a seal is obtained all the way around against the wall of the auditory canal.

A channel 4 (see FIG. 2) is present in the central part of the sealing body 2, which channel in use forms an air communication between the auditory canal and the open environment. The channel 4 comprises a distal end part at the side of the auditory canal and a proximal end part at the side of the open environment. The channel 4 comprises a widened part at the proximal end. A muffling device 3 is placed in this widened part 5.

The muffling device 3 comprises a tubular housing element 6, which is fitted in the widened part 5 and rests with an outward directed flange 8 against the end of the widened part 5. The flange 8 ensures that the housing element 6 cannot be pressed further into the channel 4. The flange 8 is provided on the periphery with eight lips 9, uniformly distributed along the periphery, and each provided with an inward directed snap groove 10.

The part of the relatively rigid housing element 6 which is placed in the widened part 5 has an external diameter which is slightly larger than the internal diameter of the widened part 5. When the relatively rigid housing element 6 is placed in the flexible widened part 5, a close fit of the housing element in the widened part 5 will be produced, so that the housing element 6 will stay in position in the widened part 5 during use of the hearing protector 1.

Figure 4:
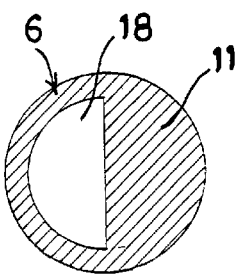
FIG. 4 is a view in cross section along the line IV—IV in FIG. 2, in which view the sealing device being omitted.

At the end facing the channel 4, the housing element 6 is provided with an end wall 11, in which a through aperture 18 is provided. The through aperture 18 is formed here by breaking through half of the end wall 11 (see FIG. 4).

A tubular control element 7 is placed in the housing element 6. The control element 7 has a muffling part projecting into the housing element 6, and a control part projecting outside the housing element 6. The control part is widened in the radial direction relative to the muffling part. The control part is provided with a snap edge 12, which engages in the snap grooves 10 of the lips 9 when the control element 7 is inserted into the housing element 6, with the result that the control element 7 is locked against axial displacement relative to the housing element 6. Fixing the control element in the axial direction relative to the housing element can also be carried out in another way. The embodiment with the snap edge 12 has the advantage that not only is the control element 7 fixed in the axial direction in the housing element 6, but replacement of the control element 7 by another control element 7, for example with other muffling values, can also be carried out easily if necessary. The control element 7 and the housing element 6 fit rotatably into each other. The control part serves as a knob which can easily be taken between the fingers, in order to rotate the control element 7 relative to the housing element 6, thus setting the muffling value of the muffling device 3.

Figure 3:
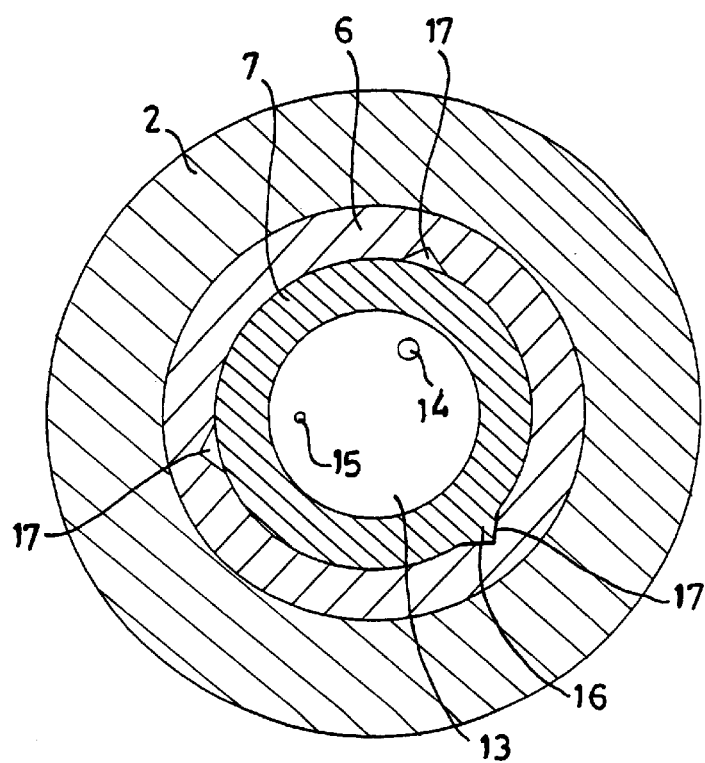
FIG. 3 is a view in cross section on an enlarged scale along the line III—III in FIG. 2.

The control element 7 is provided with an end wall 13 at the end facing the channel 4. The end wall 13 is provided with two through apertures 14, 15 with different diameters (see FIG. 3). The diameters of the through apertures 14 and 15 are small compared with the diameter of the channel 4, and are, for example, approximately 0.3 and 0.1 mm. The small through apertures ensure a good sound reduction, while ensuring that voice sounds are still audible.

A muffling device with three different muffling values is thus obtained, namely the muffling values belonging to the through apertures 14 and 15 and a maximum muffling value belonging to a rotational position of the control element 7 in the housing element 6, where no air communication is present between the auditory canal and the environment by way of the channel 4. In the case of the maximum muffling value, the two through apertures 14 and 15 are situated opposite the part of the end wall 11 of the housing element 6 which is without through apertures.

The through apertures 14 and 15 and the position with the maximum muffling value are situated at equal angular distances from each other. In addition, the through apertures 14 and 15 and the position with the maximum muffling value are situated on a circle in the example shown, but this is not necessary. In a variant, several through apertures are provided in the housing element and one through aperture in the control element.

The elements 6, 7 are provided with complementary position-indicating means. A projection 16 is provided on the outside wall of the muffling part. The projection 16 interacts with three recesses 17 present in the inside wall of the housing element 6 (see FIG. 3). The recesses 17 are placed at the same angular distances from each other as the through apertures 14 and 15 and the position with maximum muffling. In the example shown, the projection 16 engages on the side of the position with the maximum muffling value by snapping or clicking into one of the recesses 17. By means of elastic deformation of the projection 16, when the control element 7 is rotated, a "clicking force" must be overcome in each case in order to move the projection 16 into one of the other recesses 17. The rotational position in which the control element 7 is situated is preferably marked on the outside of the control part.

Figure 2:
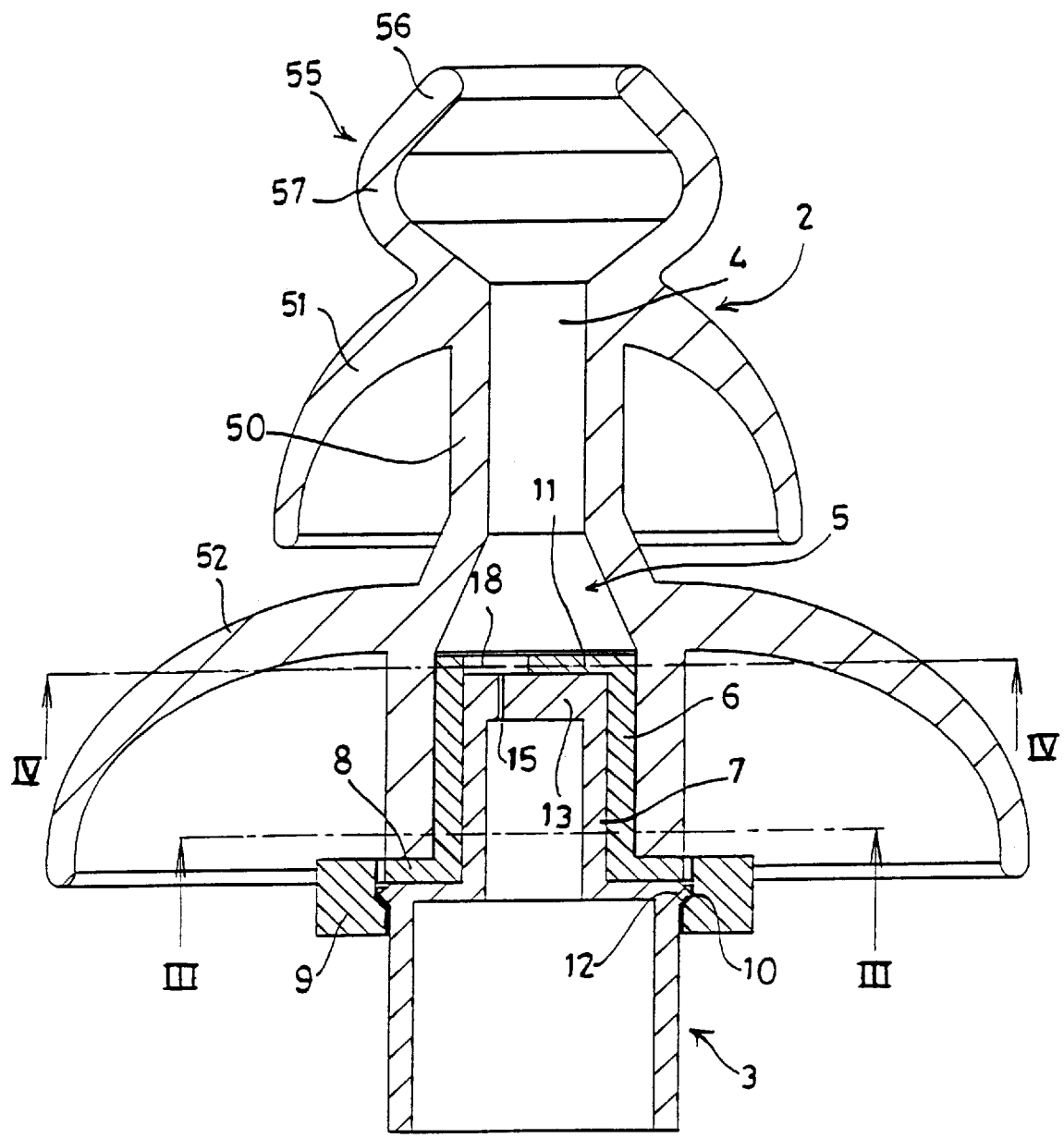
FIG. 2 is a view in longitudinal section of FIG. 1.

The operation of the muffling device 3 will be explained below with reference to FIG. 2.

In the rotational position of the control element 7 relative to the housing element 6 shown in FIG. 2, the through aperture 15 in the end wall 13 is situated below the through aperture 18 in the end wall 11. This means that the channel 4, and consequently the auditory canal of the user, has an air communication with the environment by way of the through aperture 15. The muffling device 3 in this position has a muffling value which corresponds to the through aperture 15. When the control element 7 is subsequently rotated from the rotational position shown in FIG. 2 in an anticlockwise direction until the projection 16 engages in the next recess 17, the through aperture 14 comes to rest below the through aperture 18. In this way the muffling device 3 is set at a muffling value corresponding to the through aperture 14. On further rotation of the control element 7, a part of the end wall 13 without through aperture subsequently comes to rest below the through aperture 18, with the result that no air communication is present between the auditory canal of the user and the environment by way of the channel 4. The muffling device 3 has then been set at the maximum muffling value.

Although three discrete rotational positions with corresponding muffling values are given in the exemplary embodiment described above, it is clear that more rotational positions with corresponding muffling values can be provided, for example by providing more through apertures in the end wall of the control element. It is then best to make the through aperture in the housing element smaller, so that in each case only the desired through aperture(s) of the control element come to rest in an overlapping relationship with the through aperture in the housing element.

The relatively rigid muffling device 3, which is made of, for example, PP or POM, advantageously provides the sealing body 2 with a certain rigidity. This means that the hearing protector 1 can be inserted more easily into the auditory canal, while the muffling device can also be easily controlled by hand.

Figure 5:
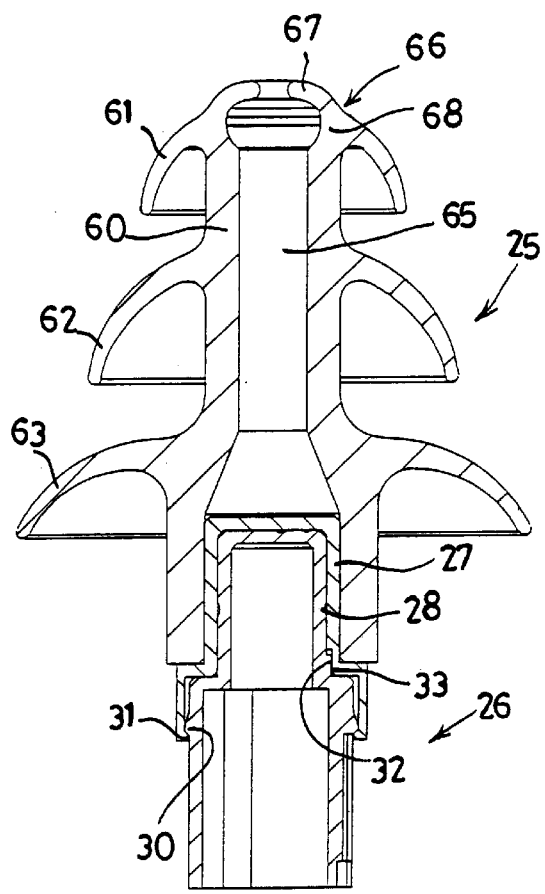
FIG. 5 is a view in longitudinal section of a second embodiment of a hearing protector according to the invention.
Figure 8:
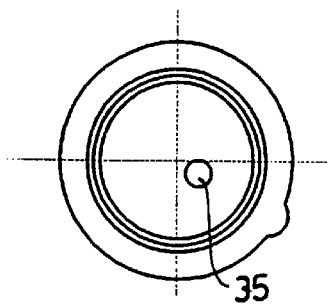
FIG. 8 is a top view of FIG. 7.
Figure 6:
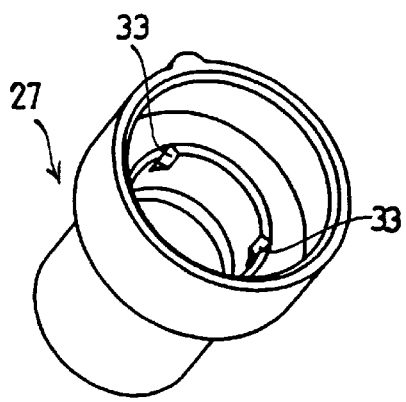
FIG. 6 is a view in perspective of the housing element of the muffling device in FIG. 5.
Figure 7:
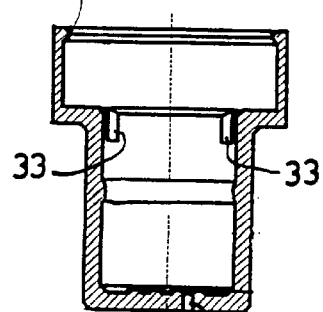
FIG. 7 is a view in longitudinal section of FIG. 6.
Figure 9:
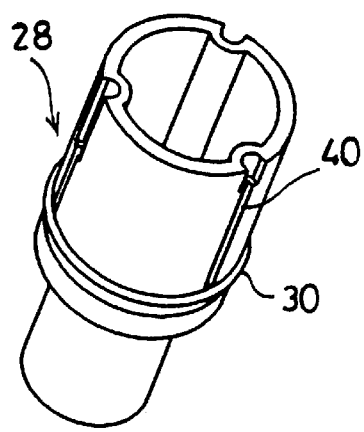
FIG. 9 is a view in perspective of the control element of the muffling device in FIG. 5.
Figure 10:
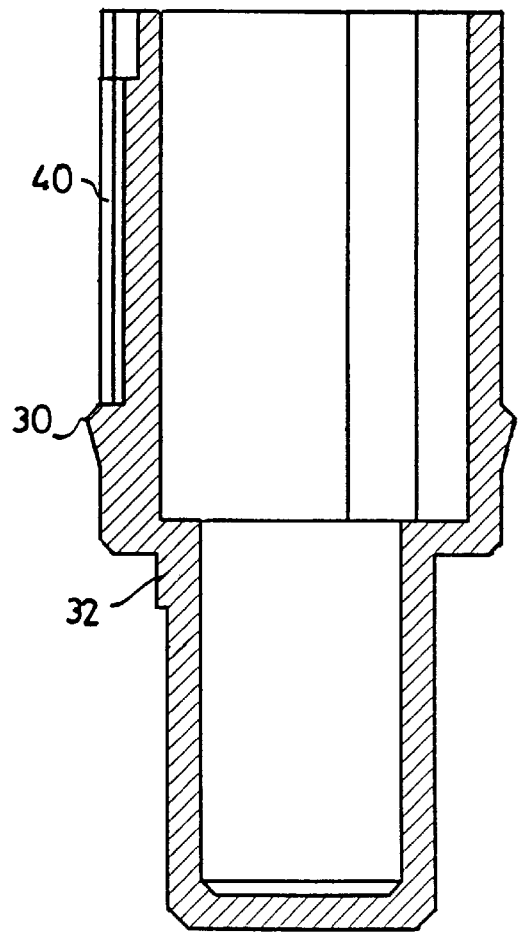
FIG. 10 is a view in longitudinal section on an enlarged scale of FIG. 9.
Figure 12:
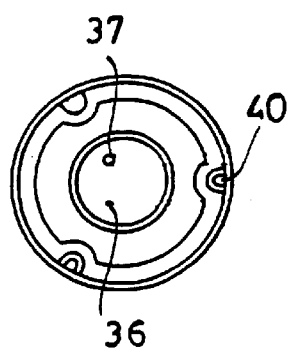
FIG. 12 is a top view of FIG. 11.
Figure 11:
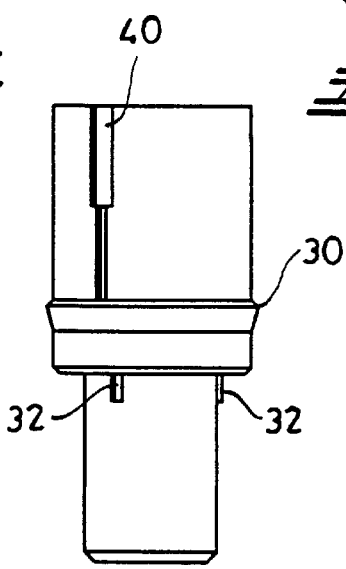
FIG. 11 is a front view of FIG. 9.

The hearing protector in FIG. 5 comprises a sealing body 25 and a muffling device 26. The sealing body will be explained in greater detail below. The muffling device 26 is, on the whole, the same as the muffling device 3 in FIGS. 1–4, and again comprises a tubular housing element 27 and a tubular control element 28. The elements 27, 28 engage rotatably in each other, in which an axial locking is ensured by two interacting snap edges 30, 31. Three recesses 33 and projections 32 distributed along the periphery are provided on the housing element 27 and the control element 28 respectively. The recesses 33 and the projections 32 together form the complementary position-indicating means.

For the sake of clarity, the housing element 27 and the control element 28 are shown separately in FIGS. 6–8 and FIGS. 9–12 respectively. The housing element 27 is provided with one through aperture 35 in its end wall (see FIG. 7, 8). The control element 28 is provided with two through apertures 36, 37 in its end wall (see FIG. 12). The through aperture 35 here is a round recess with a relatively small diameter. The through aperture 35 is situated on the same radius as the through apertures 36, 37.

The control element 28 is provided with three grooves 40 extending in the axial direction on its control part. Said grooves 40 contribute to a better grip of a user on the control part. The grooves 40 each have a widened part on their free end. The individual widened parts have differing depths, by means of which the rotational position in which the control element 28 is situated can be established. For example, the greatest depth goes with the smallest muffling value.

Although in the drawing a hearing protector having a combination of an adjustable muffling device with a sealing body of the type for universal use is shown, the hearing protector can also comprise an otoplastic.

The adjustable muffling devices described above are suitable in particular for use with sealing bodies of the type for universal use. In the case of the embodiment according to the invention in FIGS. 1 and 2, the sealing body 2 is made of a flexible, elastic material, which is, furthermore, suitable for multiple use of the hearing protector over a longer period of time of, for example, several years. The manufacture of the sealing body 2 can be carried out by, for example, injection moulding.

The sealing body 2 comprises a central tube 50, which bounds the through channel 4 with a wall. Two shells 51 and 52 are provided on the central tube 50. In use, the shells 51 and 52 rest against the wall of the auditory canal of the user and against the opening edge of the auditory canal respectively.

The distal end part of the channel 4 is bounded by an end wall 55. The end wall 55 comprises an end edge part 56, which is bent inwards in the radial direction. Under a load, the end edge part 56 will deform in the axial direction and be pressed inwards. The end wall 55 further comprises a central part 57, which is formed curving outwards in the radial direction. The distal end part of the channel 4 bounded by the end wall 55 is widened in a correspondingly spherical shape.

At the place where the wall of the central tube 50 merges into the end wall 55, the shell 51 connects to the outer periphery of the tube 50. The shell 51 is designed like a parachute, the concave side facing the proximal end part of the channel 4.

Further engaging upon the outer periphery of the wall of the tube 50 is the second parachute-like shell 52, which is situated closer to the proximal end part, and the concave side of which likewise faces the proximal end part. The dimensions of the second shell 52 are such that said shell comes to rest in a sealing manner against the opening edge of an auditory canal. The shell 52 thus ensures that the sealing body is not inserted too far into the auditory canal.

When the sealing device 2 is being placed in the auditory canal of a user, the end wall 55 will be stopped in the axial direction on its end edge part 56. The ensuing axial deformation of the end edge part 56 ensures that the central part 57 will expand in the radial direction, with the result that the central part 57 will come to rest in a sealing manner against the wall of the auditory canal. With this the radial dimensions of the central part 57 are selected in such a way that the sealing device 2 is easy to place in the auditory canal.

The specific deformation of the front part of the sealing body ensures that irritating pressure points in the auditory canal of the user are prevented, and the sealing body placed in the auditory canal will generally feel comfortable. The user will consequently be less inclined to remove the hearing protector from the auditory canal while being exposed to excessive noise. The spherical central part also seals off very well against the wall of the auditory canal.

FIG. 5 shows a second embodiment of a sealing body. The sealing body 25 comprises a central tube 60, on which three shells 61, 62 and 63 are provided. The tube 60 bounds a channel 65, which is widened in a spherical shape at the distal end part. The channel part widened in a spherical shape is bounded by an end wall 66 with an end edge part 67 bent inwards in the radial direction. The end edge part 67 will deform elastically in the axial direction under an axial pressure load. The end wall 66 further comprises a central part 68, to which the first shell 61 directly connects. The first shell 61 and the end wall 66 have a lower thickness than the thickness of the wall of the tube 60. If the end edge part 67 deforms, the first shell 61 can then deform outwards slightly in the radial direction.

Figure 13:
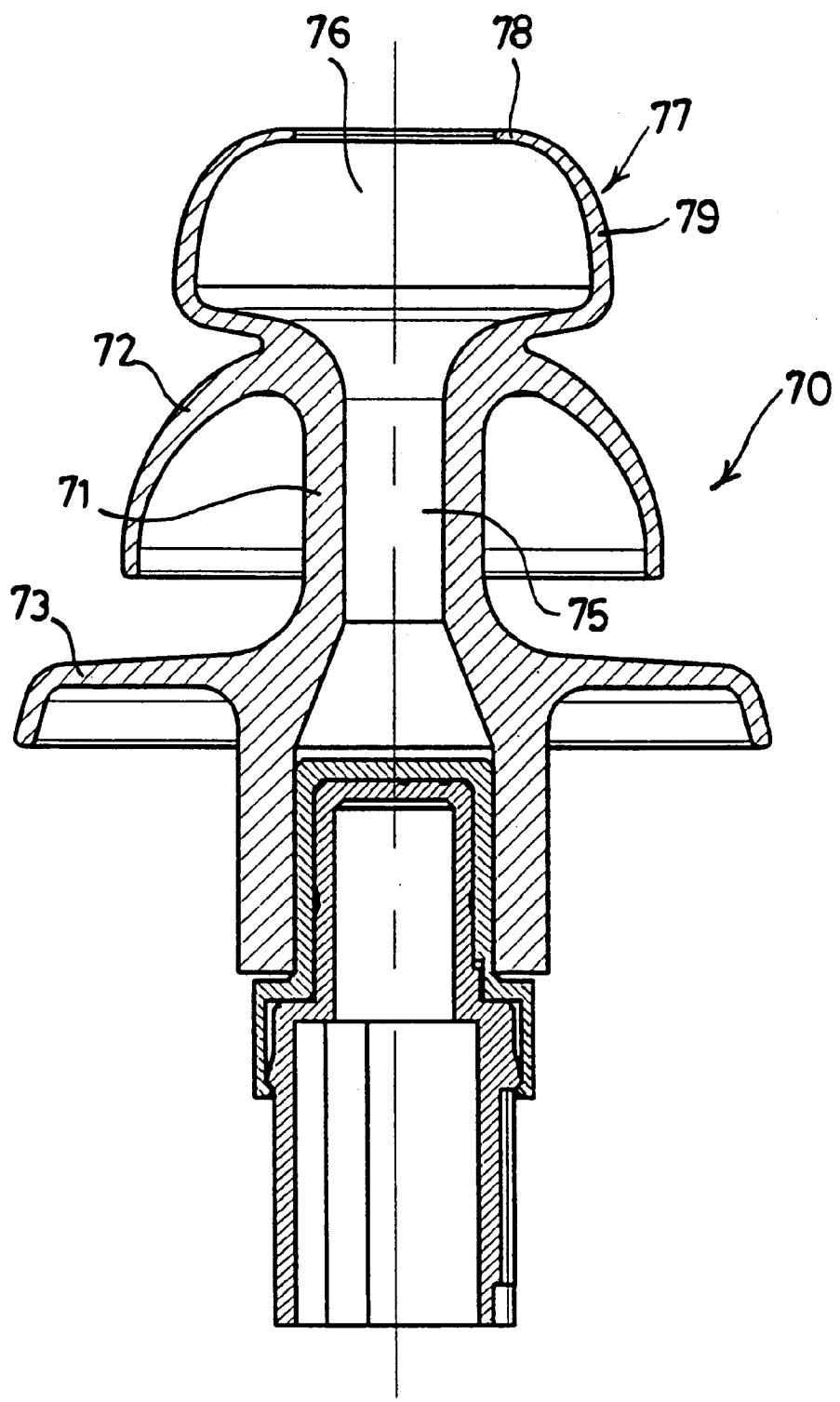
FIG. 13 is a view in longitudinal section of a third embodiment of a hearing protector according to the invention.

FIG. 13 shows a third embodiment of a sealing body. The sealing body 70 comprises a central tube 71, on which two shells 72 and 73 are provided. The tube 71 bounds a channel 75. The front part of the channel 75 opens out into an open chamber 76. The open chamber 76 is bounded by an end wall 77 with an end edge part 78 bent inwards in the radial direction. The end wall 77 has a smaller thickness than the tube 71. The end wall 77 further comprises a central part 79 with a substantially constant radial measurement. This ensures that during insertion into an auditory canal the front part of the sealing body is being less flattened than is the case with the embodiment in FIG. 1, making the insertion slightly easier. The end edge part 78 can still deform elastically in a simple manner in the axial direction under an axial pressure load.

Thus the invention provides sealing bodies which feel comfortable in the ear without in the process exerting too great pressure on certain points in the auditory canal. The shape is suitable for universal use. Surprisingly, it has been found in practice that the muffling characteristics of the sealing body are very consistent with the muffling characteristics of the muffling device according to the invention. This is probably due to the widened distal end part of the channel which is partly bounded by the end edge part of elastically deformable material bent inwards in the radial direction. However, the sealing body according to the invention can also be used in combination with other muffling devices.

In this way, the invention provides a hearing protector with a simple stepwise adjustable muffling device in combination with a universal sealing body which is extremely comfortable to wear, while the muffling characteristics of the hearing protector as a whole meet both the requirements and the statutory standards.

What is claimed is:

1. A hearing protector for placing in an auditory canal of a user, comprising: a sealing body with a channel extending therethrough; and a muffling device which is connected to said sealing body and connects to said channel;

whereby said sealing body is to be placed in the auditory canal with said channel extending between the auditory canal and the atmosphere, in which said channel has a distal end part at the side of the auditory canal and a proximal end part at the side of the atmosphere; and;

wherein said muffling device connects to said proximal end part of said channel and comprises a rotatable control element, which control element is provided with at least one through aperture, said muffling device further comprising a housing element, which housing element is provided with at least one through aperture;

said control element and said housing element being rotatable relative to each other between two or more discrete rotational positions with corresponding muffling values, with the result that said apertures in said control element and in said housing element overlap each other to a greater or lesser extent depending on a mutual angle of rotation, wherein said control element and said housing element are provided with complementary position-indicating means for indicating said two or more discrete rotational positions, said complementary position-indicating means comprising parts which through a rotation of said control element and said housing element relative to each other snap or click into each other.

2. The hearing protector according to claim 1, wherein said complementary position-indicating means comprise at least one projection on said control element and at least two recesses in said housing element, the number of recesses and the positions thereof corresponding to the number of discrete rotational positions with corresponding muffling values.

3. The hearing protector according to claim 1, wherein said control element comprises several through apertures, said several through apertures having different diameters.

4. The hearing protector according to claim 1, wherein in one of the discrete rotational positions indicated by said complementary position-indicating means there is no overlap of through apertures in said control element and in said housing element.

5. The hearing protector according to claim 4, including two through apertures of different diameter in said control element, and three recesses in said housing element.

6. The hearing protector according to claim 1, wherein the diameter of said through aperture in said control element is small compared with the diameter of said channel in said sealing body.

7. A hearing protector according to claim 1, wherein said sealing body with said channel extending through it further comprises:

a central tube having a wall bounding said channel;

at least a first shell provided on said tube and designed to rest in a sealing manner against an auditory canal; and an end wall bounding said distal end part of said channel and having an end edge part of an elastically deformable material which is bent inwards in the radial direction, which end edge part is elastically deformable in an axial direction under an axial pressure load, as a result of placing said sealing body in an auditory canal.

8. The hearing protector according to claim 7, wherein said distal end part of said channel is spherical, said end wall having a central part connecting to said inward bent end edge part, which central part is designed in a spherical shape in a radial direction.

9. The hearing protector according to claim 8, in which a deformation of said end edge part in the axial direction causes said central part to deform outwardly in the radial direction.

10. The hearing protector according to claim 7, wherein said first shell connects to said end wall.

11. A hearing protector according to claim 7, wherein a second shell is provided, which second shell has a greater radial measurement than said first shell and connects to said tube, and is designed to rest against an opening edge of the auditory canal.

12. A hearing protector according to claim 7, wherein the thickness of said end wall is smaller than the thickness of said tube.

* * * * *